(12) United States Patent
Day et al.

(10) Patent No.: US 6,217,797 B1
(45) Date of Patent: Apr. 17, 2001

(54) SYNTHESIS AND USE OF AMINE MOLYBDATES

(75) Inventors: James F. Day, Winston-Salem; Chad E. Lee, Kernersville, both of NC (US)

(73) Assignee: Unitex Chemical Corporation, Greensboro, NC (US)

(*) Notice: Subject to any disclaimer, the term of this patent is extended or adjusted under 35 U.S.C. 154(b) by 0 days.

(21) Appl. No.: 09/547,139

(22) Filed: Apr. 11, 2000

(51) Int. Cl.⁷ .............................. C09K 21/00; C07F 11/00
(52) U.S. Cl. .............................. 252/609; 544/181; 556/57
(58) Field of Search .............................. 544/181; 556/57; 252/609

(56) References Cited

U.S. PATENT DOCUMENTS

| | | | |
|---|---|---|---|
| 4,053,455 | * 10/1977 | Kroenke | 260/45.75 R |
| 4,153,792 | 5/1979 | Kroenke | 544/181 |
| 4,217,292 | 8/1980 | Kroenke | 260/429 |

* cited by examiner

Primary Examiner—Porfirio Nazario-Gonzalez
(74) Attorney, Agent, or Firm—Robert H. Berdo

(57) ABSTRACT

There is disclosed an amine molybdate obtained by reacting an amine with molybdenum trioxide in an aqueous acidic solution under pressure and at a temperature of from 105–150° C.

10 Claims, No Drawings

SYNTHESIS AND USE OF AMINE MOLYBDATES

BACKGROUND OF THE INVENTION

Vinyl chloride and vinylidene chloride polymers are known to be self-extinguishing and relatively more flame retardant than other polymers such as polyethylene, polypropylene and the like. However, a substantial amount of smoke may be produced upon exposure of vinyl chloride and vinylidene chloride polymers to a flame. The fact that an additive is a flame retardant does not necessarily mean that it will have good smoke retardant properties.

Inorganic and organometallic complexes of molybdenum are commercially useful as smoke suppressants in halogenated resins. Various amine molybdates have been investigated by B. F. Goodrich, see U.S. Pat. No. 4,153,792, for smoke suppression in PVC compounds. These compounds were plagued with poor performance properties due to residual molybdenum trioxide. The residual $MoO_3$ causes blue discoloration of the resin systems coupled with poor thermal stability.

The most commercially recognized material for smoke suppression in PVC is ammonium octamolybdate (AOM). AOM is the premium material to make low smoke PVC compounds, particularly for plenum wire and cable applications. AOM is used in numerous PVC jacket formulations that pass the rigorous UL910 test for cables (cooper conductor and fiber optic cables).

U.S. Pat. No. 4,153,792 discloses the production of amine molybdates, especially melamine molybdate by reacting an amine, such as melamine, with molybdenum trioxide in an aqueous acidic medium under reflux.

U.S. Pat. No. 4,217,292 discloses the production of amine molybdates, preferably melamine molybdate by reacting an amine such as melamine with a stoichiometric quantity of molybdenum trioxide in an aqueous medium in the presence of an ammonium salt. The aqueous medium is essentially free of acid. The reaction may be conducted at temperatures within the range of 75–110° C.

SUMMARY OF THE INVENTION

It has now been discovered that an amine molybdate which contains no residual molybdenum trioxide may be prepared by reacting an amine, preferably melamine, with molybdenum trioxide in an acidic aqueous medium under greater than atmospheric pressure and at a temperature of from 105–150° C. The reaction is conducted for a time sufficient to eliminate all detectable amounts of molybdenum trioxide. The resultant salts are highly effective as smoke retardants in vinyl chloride and vinylidene chloride polymers and in fluoropolymers. These salts are a snow white powder which do not discolor the halogenated resins when they are compounded with such resins. In contrast, the prior art salts are blue to gray tinted and this color is imparted to the compounded chlorinated resin.

DETAILED DESCRIPTION OF THE INVENTION

Amine molybdates are produced in accordance with this invention by reacting essentially stoichiometric quantities of molybdenum trioxide with an amine in an aqueous acidic medium, preferably containing a water soluble ammonium salt of a monovalent or divalent acid. The reaction is conducted at a temperature of 105–150° C., and, preferably, at a temperature of 115–150° C. under a pressure of up to 6 bar. Preferably, the pH of the reaction mixture is within the range of 5–7.

Amines suitable for preparing the amine molybdates using the process of this invention include polymeric amines, as well as simple amines. The simple amines may contain from 1 to 75 carbon atoms and from 1 to 10 primary, secondary, or tertiary amine groups or a mixture thereof, more preferably from 1 to 6 groups. Simple amines include aliphatic, alicyclic, aromatic and heterocyclic amines. Examples of suitable polymeric amines include polyethyleneimine, polyvinylpyridine, polyvinylpyrroilidine and poly(2,24-trimethyl-1,2-dihydroquinolyl). Examples of suitably simple amines include aliphatic amines such as ethylamine, ethylenediamine, 1,2-propanediamine, 1,3-propanediamine, 1,4-butanediamine, 2-methyl- 1,2-propanediamine, 1,5-pentanediamine, 1,6-hexanediamine, 1,7-heptanediamine, 1,8-octanediamine, 1,10-decanediamine, 1,12-dodecanediamine, and the like. Also suitable are aliphatic amines such as diethylenetriamine, triethylenetetramine, tetraethylenepentamine, bis(hexamethylene)triamine, 3,3'-iminobispropylamine, guanidine carbonate, and the like. Other suitable amines include alicyclic diamines and polyamines such as 1,2-diaminocyclohexane, 1,8-p-menthanediamine, and the like, aromatic amines such as aniline, N,N-dimethylaniline, and the like, and heterocyclic amines such as melamine and substituted melamines, ammeline, pyridene, piperazine, hexamethylenetetramine, 2,2,4-trimethyldecahydroquinoline, and N-(aminoalkyl)-piperazines wherein each alkyl group contains from 1 to 12 carbon atoms, more preferably 1 to 6 carbon atoms, such as N-(2-aminoethyl)-piperazine and the like.

The amine molybdates of this invention are useful as smoke suppressants in vinyl halide resins (PVC, PVDF, PTFE, PVDC, CPVC, and ECTFE resins), by a reductive coupling mechanism which induces char formation.

EXAMPLE 1

Melamine octamolybdate is prepared by charging a 50 gallon reactor with 292 pounds of deionized water. The agitator is started and 9.37 pounds of glacial acetic acid are added followed by 9.69 pounds of aqueous ammonium hydroxide. The pH measured as is should be 5–7. A slightly acidic pH is required. There are then added 9.69 pounds of melamine and 22.14 pounds of molybdenum trioxide. The reactor is sealed and heated to 135° C. under pressure for three hours. The product slurry is initially blue and eventually turns white after all the molybdenum trioxide has been eliminated. The reactor is cooled to 20–30° C. and the reaction mass is filtered. The filter cake is washed with deionized water to neutrality. The product is dried under vacuum at 135° C. until less than 0.05% water by weight is achieved as measured by Karl Fischer titration. The dried product is micronized with an air jet mill to an average particle size of 2 microns. The finished product is snow white in color with no free molybdenum trioxide as determined by x-ray diffraction analysis.

In contrast, when Example 1 is repeated using reflux instead of heating at 135° C. for 1 to 48 hours, there is obtained a product with a slight blue cast with residual molybdenum trioxide ranging from 0.68 to 2.3% by weight. This product is designated in the following tables as "comparative example".

The following examples illustrate the use of the molybdenum octamolybdate obtained by the practice of this invention.

EXAMPLE 2

Molybdenum octamolybdate is compounded into rigid PVC at 200° C. with Geon 30 PVC, 2 phr Microthene 510 Lubricant, 2 phr tin thioglycolate stabilizer and 2 phr melamine octamolybdate obtained as described in Example 1. The compound is compression molded and subjected to various tests with the results tabulated in Table 1.

TABLE 1

RIGID PVC COMPOUNDS

| Example | Loading (phr) Molybdenum compound | Thermal Stability (5% Loss TGA) | Compound Thermal Stability (min) | Oxygen Index | % Smoke Reduction (Dmc in ASTM E-662) |
|---|---|---|---|---|---|
| Control | None | — | >120 | 45 | — |
| Unitex Invention | 2 | 380° C. | >120 | 49 | 87 |
| Comparative Example | 2 | 245° C. | 28 | 46 | 55 |

EXAMPLE 3

Flexible PVC (Geon 30) compounds are prepared by dry blending additives with Geon 30 PVC and then compounding in a two roll mill at 160° F. The compounds are compression molded and tested. The results are tabulated in Table 3. The general purpose formula used is set forth in Table 2.

TABLE 2

| MATERIAL | LOADING (phr) |
|---|---|
| Geon 30 PVC | 100 |
| Tris(2-Ethylhexyl)Trimellitate | 34 |
| Di(2-Ethylhexyl)Tetrabromophthalate | 40 |
| Molybdate Complex of Example 1 | 2.5 |
| Antimony Trioxide | 2 |
| Lead Stabilizer (Dythal XL) | 7 |

TABLE 3

Flexible PVC Compounds

| Example | Loading (phr) Molybdenum compound | Thermal Stability (5% Loss TGA) | Compound Thermal Stability (min) | Oxygen Index | % Smoke Reduction (Dmc in ASTM E-662) |
|---|---|---|---|---|---|
| Control | None | — | >120 | 34 | — |
| AOM | 2.5 | 290° C. | >120 | 36 | 35 |
| Compound of Example 1 | 2.5 | 380° C. | >120 | 38 | 20 |
| Comparative Example | 2 | 245° C. | 18 | 35 | 10 |

EXAMPLE 4

Flexible PVC (Geon 30)-PVDF(Kynar Flex 3120-50) compounds are prepared by dry blending additives with the resins and then compounding in a two roll mill at 180° F. The compounds are compression molded and tested. The results are tabulated in Table 5. The general purpose formula is set forth in Table 4.

TABLE 4

| MATERIAL | LOADING (phr) |
|---|---|
| Geon 30 PVC | 50 |
| Kynar Flex 3120 | 50 |
| Di(2-Ethylhexyl)Tetrabromophthalate | 30 |
| Molybdate Complex of Example 1 | 2.5 |
| Lead Stabilizer (Dythal XL) | 7 |

TABLE 5

Flexible PVC-PVDF Compounds

| Example | Loading (phr) Molybdenum compound | Thermal Stability (5% Loss TGA) | Compound Thermal Stability (min) | Oxygen Index | % Smoke Reduction (Dmc in ASTM E-662) |
|---|---|---|---|---|---|
| Control | None | — | >120 | 39 | — |
| AOM | 2.5 | 290° C. | 8 | 36 | — |
| Compound of Example 1 | 2.5 | 380° C. | >120 | 42 | 30 |
| Comparative Example | 2.5 | 245° C. | 14 | 35 | 10 |

It is apparent that significant smoke reduction is accomplished (up to 80% reduction) by the addition of 0.01 to 30% by weight of melamine molybdate prepared in Example 1. None of the resins compounded with the melamine molybdate prepared in Example 1 showed any discoloration.

We claim:

1. A process for the preparation of an amine molybdate which comprises reacting an amine with molybdenum trioxide in an aqueous acidic medium under pressure at a temperature of from 105–150° C. and continuing the reaction until all detectable amounts of molybdenum trioxide have been eliminated.

2. The process of claim 1 wherein said amine is melamine.

3. The process of claim 1 wherein the reaction is conducted at a temperature of from 115–150° C.

4. The process of claim 1 wherein the reaction is conducted in the presence of an ammonium salt of a monovalent or divalent acid.

5. An amine molybdate obtained by the process of claim 1.

6. An melamine molybdate obtained by the process of claim 2.

7. An amine molybdate obtained by the process of claim 3.

8. An amine molybdate obtained by the process of claim 4.

9. A smoke retardant composition comprising a vinyl halide or vinylidene halide polymer and a smoke retardant amount of the amine molybdate obtained by the process of claim 2.

10. A composition of claim 9 wherein said amine molybdate is present in an amount of from about 0.01 to 30 weight parts per 100 parts of polymer.

\* \* \* \* \*